United States Patent
McElvaney

(10) Patent No.: US 6,254,775 B1
(45) Date of Patent: Jul. 3, 2001

(54) ANAEROBIC DIGESTER SYSTEM AND METHOD

(76) Inventor: James D. McElvaney, 3322 Fawn Trail NE., Marietta, GA (US) 30066

( * ) Notice: Subject to any disclaimer, the term of this patent is extended or adjusted under 35 U.S.C. 154(b) by 0 days.

(21) Appl. No.: 09/262,784

(22) Filed: Mar. 4, 1999

Related U.S. Application Data
(60) Provisional application No. 60/077,574, filed on Mar. 9, 1998.

(51) Int. Cl.$^7$ .................................................. C02F 3/00
(52) U.S. Cl. ........................... 210/603; 210/605; 210/617
(58) Field of Search ................................... 210/603, 604, 210/615, 616, 617, 194, 605

(56) References Cited

U.S. PATENT DOCUMENTS

| | | |
|---|---|---|
| 4,253,271 | 3/1981 | Raymond . |
| 4,274,838 | 6/1981 | Dale et al. . |
| 4,318,993 | 3/1982 | Ghosh . |
| 4,334,997 | 6/1982 | Peterson . |
| 4,499,614 | 2/1985 | Yeagley . |
| 4,551,243 | 11/1985 | Martin . |
| 4,885,094 | 12/1989 | Srinivasan . |
| 4,956,082 * | 9/1990 | Choi . |
| 5,096,579 | 3/1992 | Jordan . |
| 5,338,452 * | 8/1994 | Pidaparti . |
| 5,403,742 | 4/1995 | Freeman . |
| 5,413,713 | 5/1995 | Day . |
| 5,499,770 | 3/1996 | McCullough . |
| 5,500,123 | 3/1996 | Srivatsa . |
| 5,500,306 | 3/1996 | Hsu . |
| 5,512,474 | 4/1996 | Clapper . |
| 5,525,228 * | 6/1996 | Dague et al. . |
| 5,525,229 | 6/1996 | Shih . |
| 5,580,644 * | 12/1996 | Minami . |
| 5,585,086 | 12/1996 | McCullough . |
| 5,618,412 | 4/1997 | Herding . |
| 5,630,942 * | 5/1997 | Steiner . |

OTHER PUBLICATIONS http://www.bioconverter.com/about.htm, downloaded and printed on Jul. 19, 2000.*
http://www.dwacaribbean.com/articles.htm downloaded and printed on Jul. 19, 2000.*

* cited by examiner

Primary Examiner—Chester T. Barry
(74) Attorney, Agent, or Firm—Leighton K. Chong

(57) ABSTRACT

An anaerobic digester system has a vertically upright vessel, a matrix arranged in the vessel supporting a microorganism biomass thereon, an input for supplying an input slurry of liquid and suspended solids at an upper portion of the vessel above the matrix, a gas output at the top of the vessel for withdrawing gas generated by anaerobic digestion of solids, and an effluent output at the bottom of the vessel for withdrawing liquid and remaining solids. The vessel has a preferred liquid height to diameter ratio of 2 to 1, and is constructed of inert fiberglass-reinforced plastic coated with a translucent blue gel pigment layer for filtering light at wavelengths that promote biomass cultivation. The matrix is formed as an array of panels mounted to a spindle with wheels fixed at spaced intervals along its vertical height, and the panel are made of a polyethylene grass matting providing a high surface area to volume ratio of at least 20 to 1. Gas from the top of the vessel is recycled to the bottom to generate bubbles for mixing the feedstock. The related method of anaerobic digestion includes comminuting input wastes with a slurry grinder into a pumpable slurry 8–10 % by weight solids, and providing as the biomass hydrolytic bacteria, and fermentative bacteria including acetogenic and methanogenic bacteria to produce a methane gas product. Other products include an organic soil additive, bacterial solids plant food, and a filtrate used as plant tonic.

8 Claims, 5 Drawing Sheets

ANAEROBIC DIGESTER SYSTEM AND METHOD

This U.S. patent application claims the benefit of the filing date of U.S. Provisional Application No. 60/077,574 of the same inventor, filed on Mar. 9, 1998.

TECHNICAL FIELD

This invention generally relates to bioconversion of wastes to useful products, and more particularly, to an anaerobic digester system and method having improved performance.

BACKGROUND OF THE INVENTION

Bioconversion refers to the conversion of organic materials (generally wastes) into useful byproducts by processes (such as fermentation) involving living organisms. Bioconversion is also generically known as anaerobic digestion (AD), which is a process commonly utilized for pollution control in municipal sewage treatment and livestock waste handling. Bioconversion technology can also be applied to other organic "waste" streams, which might not otherwise be "treated" or "treatable". Some examples of these types of waste are: pre- and post-consumer food waste, "green" waste (cut grass, shrub and tree trimmings, etc.), waste paper (magazines and junk mail, mixed residential, etc.), FOG wastes (fats, oils, and grease), and "high-strength" wastewaters.

In anaerobic digesters, digestion rates are reduced due to the lack of enzymes necessary for complete digestion. This lack of enzymes can be attributed to: (1) poor growth of the bacteria which produce these enzymes; (2) the lack of access of the appropriate and acclimated bacteria to the feedstock; (3) feedback inhibition of enzyme production due to byproducts in intimate contact with the bacterial cells; and (4) inhibition of enzyme production can be due to high concentrations of byproduct intermediates in the fermentation fluid. Low rates of digestion can also be due to fresh feedstock slurry displacing the slurry of settled aggregates of active enzyme-producing bacteria, and those bacteria attached to the digested solids.

Low digestion rates can be overcome by recycling large volumes of effluents high in suspended acclimated bacterial biomass with the new input, or by recirculation of effluent, five to six times the volume of fresh input. However, this approach increases the total hydraulic retention time, and thereby, increases the working volume for the total digestion system. This in turn, requires additional vessel construction to accommodate the added volume necessary for recycle, and adds additional capital costs for that construction and operating costs to accommodate the energy and pumps used for pumping said recirculation volume.

A more efficient means of digestion can be attained by the incorporation of bacterial immobilization. The prior art has shown various approaches to the use of immobilizing matrices made of a wide range of materials. Prior art indicates that rocks, zeolites, clay particles, uncoated ceramic tile, and shaved ceramic have been used in packed bed reactors for digestion of soluble solids. Rigidly formed plastic media has been used in packed bed and anaerobic filters of soluble wastes. Heat bonded unwoven and woven fibers, and plastic films have been used in low solids digestion applications. Polyurethane foam pieces have been used in fluidized bed systems for cellular attachment to improve soluble nutrient conversion. Alginate gel beads with immobilized attached organisms within the interstices of the gel have been used in fluidized bed reactors for cellular growth and byproduct with soluble nutrients as the substrate.

The natural characteristics of microorganisms and cultured cells and how those characteristics affect immobilization have not been fully understood. Minerals, ceramics, clays and plastics with positive charged surfaces provide immobilizing surfaces for microorganisms due to attraction to negative ions which exist at the cellular surface. The known types of immobilizing surfaces, in an anaerobic filter, or packed bed reactor, can blind off or plug up with continued organism growth and subsequent attachment due to these charged effects of the individual cells. This reduces diffusion across the cell membrane, thus reducing enzyme access to substrate feedstocks and further encourages the development of aggregates of colonies filling microscopic pores and interstitial spaces of pore-related matrices. Mineral elements and metals in solution bond to the surface of these cell membranes. This adds to the overgrowth of cell populations on previous layers, resulting in blinding off of surfaces where active biomass grows.

Polyvinyl and, in particular, polyester of certain industrial types have a surface charge which is the result of polymer linkages generated in their respective manufacturing processes.

These plastic materials become irreversibly loaded with immobilized cells and with the soluble minerals extracted by immobilized cells from the fermentation liquor and are rapidly reduced in enzyme activity and cellular diffusion due to this charge effect.

Prior art digesters have employed various types of structures in an attempt to achieve high process flow and digestion rates. For example, U.S. Patent to Raymond, U.S. Pat. No. 4,274,838 to Dale, U.S. Pat. No. 4,334,997 to Peterson, U.S. Pat. No. 4,551,243 to Martin, U.S. Pat. No. 4,885,094 to Srinivasan, U.S. Pat. No. 5,096,579 to Jordan et al., U.S. Pat. No. 5,403,742 to Freeman, and U.S. Pat. No. 5,525,229 to Shih disclose horizontal fluid flow through a trough, labyrinthine, vaned, or bed-like structure. Others, such as U.S. Pat. No. 4,318,993 to Ghosh and U.S. Pat. No. 5,500,123 to Srivastava show multi-stage component vessels. U.S. Pat. No. 5,413,713 to Day et al. and U.S. Pat. No. 5,618,412 to Herding show the use of a columnar or vertical vessel with trickle-down through horizontal bed layers. U.S. Pat. No. 5,499,770 to McCullough discloses the use of a vessel with a vortex fluid flow.

While certain advantages are obtained in the use of one or another type of structure, the digesters of the prior art have not been found to achieve an optimal combination of desired digester properties, including high surface area to liquid volume ratio, high digestion rates, good immobilization of biomass, and efficient culturing and use of microorganisms.

SUMMARY OF INVENTION

In accordance with the present invention, an anaerobic digester system comprises a vertically upright vessel, a support matrix arranged in the vessel for supporting a microorganism biomass thereon, a vessel input for supplying an input slurry feedstock of liquid containing anaerobically digestible solids at an upper portion of the vessel above the matrix, a gas output from the upper portion of the vessel for withdrawing an output gas from the vessel generated by anaerobic digestion of the solids in the feedstock by the microorganism biomass, and an effluent output from a lower portion of the vessel for withdrawing liquid and remaining solids from the lower part of the vessel.

In a preferred embodiment of the digester system, the vessel has a height and diameter chosen to provide a ratio of 2 to 1 of liquid height to diameter in the vessel. The preferred vessel is formed with core, top, and base sections which are constructed of inert fiberglass-reinforced plastic. The plastic vessel sections are coated with a translucent blue gel pigment layer which filters ambient light at wavelengths above 260 nanometers and below 700 nanometers, so as to irradiate the interior of the vessel with light of wavelength desired for cultivation of the microorganism biomass.

Preferably, the matrix is formed as an array of panels mounted to a hollow spindle mounted coaxially on a central axis of the vessel. The matrix is supported on the spindle through a plurality of wheels at spaced intervals along the vertical height of the spindle. The matrix is formed with flexible planar surfaces having a three-dimensional surface architecture. These surfaces are formed with variegated surface elements that have a large combined surface area onto which the biomass material becomes attached. A particularly advantageous material is MONSANTO (™) polyethylene (artificial) grass matting (manufactured without biocide), such as are typically used for entry mats. The grass matting is applied on the matrix in long sheets across the spokes of the wheels mounted to the spindle, so as to form radial panels extending from the central spindle in the vessel. The grass matting arrayed in this fashion provides a surface area to volume ratio of at least 20 to 1.

The immobilizing matrix material is selected to be relatively charge free and manufactured of material which remains uncharged when submerged in aqueous solution. Polypropylene and polyethylene are two plastic materials having polymer chains of methyl ($CH_3$) groups or hydrogen protons (H), respectively, that can be manufactured with a low surface charge characteristic. The low surface charge avoids binding other materials that will blind off the active biomass from the digestion process.

In an improved method of anaerobic digestion in accordance with the present invention, the anaerobic digester obtains a high suspended solids digestion within the vessel by supplying liquid slurry feedstock through the vessel inlet at the upper portion of the vessel and allowing the suspended solids to flow downwardly over the biomass-supporting digester surfaces of the matrix array to the lower portion of the vessel. Recycled gas is introduced at the lower portion of the vessel to generate bubbles creating turbulence for mixing the liquid and suspended solids in the vessel. Input wastes are comminuted by a slurry grinder into a pumpable slurry. Preferably, the input slurry is 8–10% by weight (80,000–100,1000 mg per liter) solids, of which 90% are suspended solids of maximum particle size of 6–7 mm wide by 10–15 mm length.

A hydrolytic bacterial population is used as the biomass in order to produce exoenzymes or endoenzymes to hydrolyze solids in the feedstock. The biomass also includes fermentative bacteria for the conversion of the hydrolysis byproducts into intermediate compounds, including acetogenic bacteria able to convert alcohols and acids into acetate, carbon dioxide and hydrogen, and methanogenic bacteria able to convert the various byproducts of the acetogens into methane. The immobilizing matrix sustains an increased density of slow growing methanogen populations in the fermentation column. The immobilized population of bacteria increase bicarbonate alkalinity sufficient to continually digest biomass with a pH as low as 4.5, especially highly acidic fruit wastes, and no artificial pH adjustments are required.

The products of the anaerobic digester process include methane gas, which can be utilized in engine generators, cooking and/or refrigeration appliances, gas burners, and further processed as vehicle fuel, separated and dried solids which can be used as an organic soil additive, bacterial solids filtered from the liquid and dissolved solids, and a filtrate of liquid which can be used as a plant tonic.

Other objects, features, and advantages of the present invention will be explained in the following detailed description of the invention having reference to the appended drawings.

DETAILED DESCRIPTION OF INVENTION

In the present invention, an anaerobic digester vessel of improved design is provided with bacterial cell immobilizing matrices for the purpose of anaerobic digestion (bioconversion) of high suspended solids (greater than 80,000 mg/liter suspended solids by weight), and uses gas as its mixing energy in a counter current direction, under diffuse low-intensity light irradiation. The suspended solids, particulate organic wastes, especially solid wastes (the digestible fraction of municipal wastes) comprised of pre-consumer and post-consumer food wastes, including fats, oils and greases, food processing wastes, yard trimmings, leaves, and paper.

Anaerobic digesters have historically been used by municipalities for sewage biosolids digestion, by the agricultural animal byproduct industry for conversion of low solids or screened animal manure and to a limited degree by the food processing industry, for digestion of low suspended solids or high soluble solids as in anaerobic filters or upflow sludge blanket digesters. The high solids digestion afforded by the anaerobic digester of the present invention is of interest for the reduction of biodegradable and often large polymer wastes making up 70 percent of the municipal waste stream.

Digester Vessel

Figure 1:
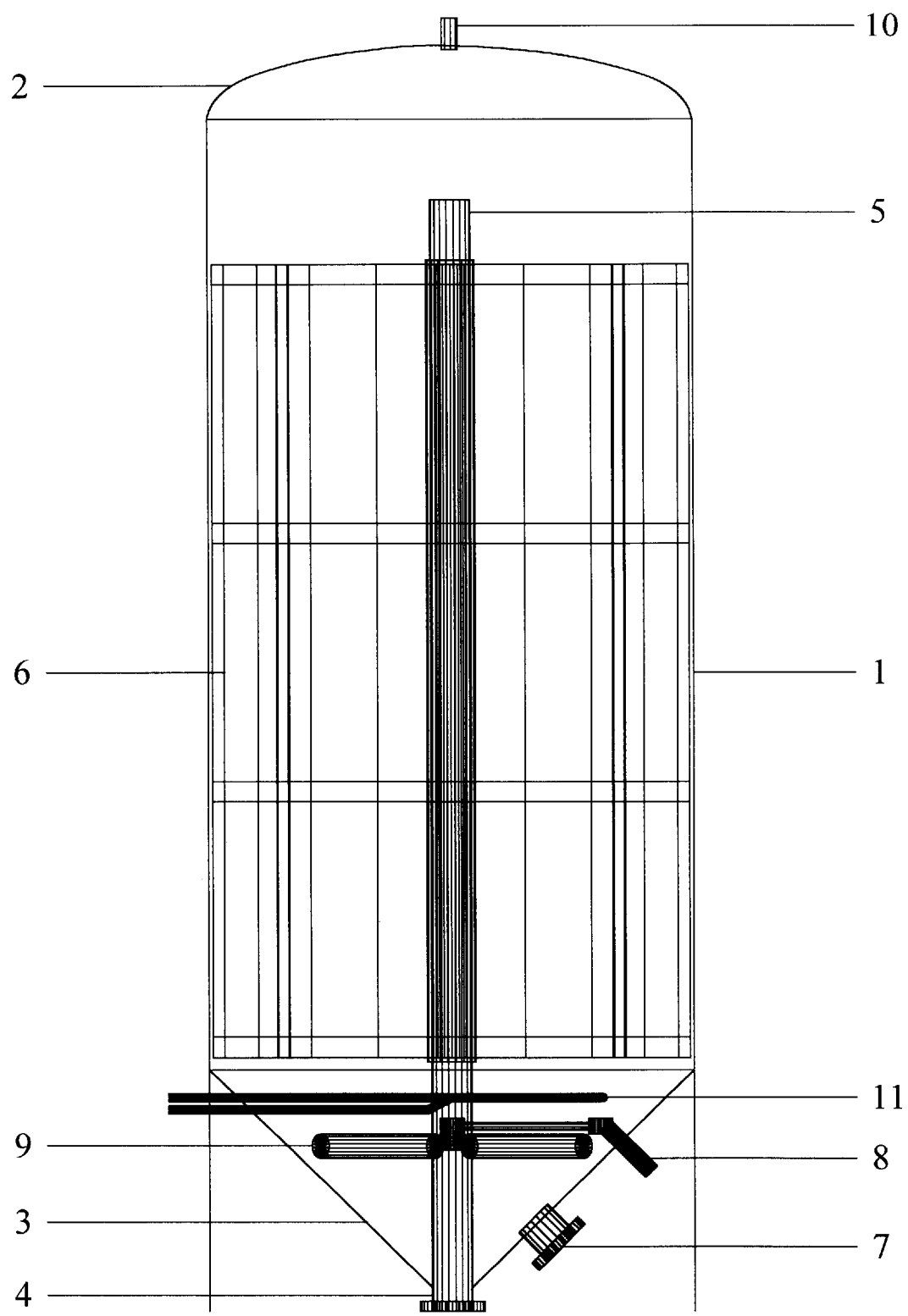
FIG. 1 is a schematic diagram of a preferred embodiment of an anaerobic digester vessel in accordance with the invention.

In FIG. 1, a preferred embodiment of an anaerobic digester is shown comprised of a vessel 1 formed by vessel walls, a cap 2, and a base 3. The vessel sections are preferably constructed of inert fiberglass-reinforced plastic, wound with resin impregnated fiberglass reinforcing fiber to a thickness of 12 mm (or about 0.375 to 0.5 inch). Within the vessel 1 is a matrix structure 6 for supporting a biomass of living organisms used in the anaerobic digestion process.

In the preferred configuration, the vessel has a height of approximately 16 feet, and diameter of 6 feet, providing for typical ratios of 2 to 1 of liquid height to diameter in the vessel. This configuration provides a liquid surface area to total volume ratio of 1 to 20 necessary for uniform dispersion of input feedstock, without the need for special nozzles for feedstock distribution. The preferred height to diameter ratio provides the optimum length of pathway for the various phases of fermentation and growth to be integrated into the same vessel, providing for metabolic and enzymatic activity related to the various states of fermentation of said solid feedstock or substrate used to encourage cellular growth and its associated enzymatic activity related to said substrate's further utilization.

At the top of the vessel is a cap 2 which serves as a gas collecting means and provides a gas-tight seal of the vessel. A gas outlet nozzle 10 (2-inch diameter) is located at the center of the cap 2. Safety relief and vacuum relief valves are connected to the gas outlet. The cap 2 is convex in shape, manufactured from fiber reinforced plastic resin of sufficient thickness and structural members to be self-supporting, and sealed at the perimeter of the surrounding walls by glass matting and resin.

The vessel base 3 is shaped in a 45-degree cone tapering from the vessel diameter of 6 feet down to the inlet nozzle 4 for s standpipe mounted on a central axis and extending into the vessel to the vessel inlet 5 positioned near the top of the vessel. The inlet nozzle 4 and vessel inlet 5 have a given diameter, e.g., 6 inches in the preferred configuration, sufficient to handle the liquids to be introduced into the vessel. A vessel outlet 7 of 6-inch is provided at one side wall a short distance, e.g., 1 foot, above the bottom of the base. A gas inlet 8, gas diffuser 9, and heat exchange coils 11 are also provided in the base 3, the functions of which are described further below. The base 3 is constructed of fiberglass and bonded with an external skirt to support the cylinder perimeter.

For the preferred operating parameters described herein, the vessel is constructed to withstand hydrostatic pressures of at least 10 psig above the static head pressure of water filled to the top. The vessel is capable of operating pressures of 5 psi and is typically operated at 1.5 psi or 30 to 40 inches (75–100 cm) of water column pressure. The vessel inlet 5 position is preferably about 30 centimeters above the top of the matrix, which in turn is approximately 30 centimeters above the operating level of the liquid in the vessel.

As one feature of the present invention, the plastic vessel sections are coated with a translucent blue gel pigment layer of approximately 1 millimeter thickness. The pigmented layer filters light at wavelengths above 260 nanometers and below 700 nanometers to irradiate through the vessel walls and top to the fermentation fluid and the exposed surfaces of the immobilizing matrix. The pigmented layer shades or otherwise limits solar irradiation to low intensity light exposure to the cellular biomass and surfaces. The addition of the blue gel layer provides the desired wavelengths of light impinging on the bacterial cells. Bright and/or full sunlight is known to inhibit photosynthetic activity in algal, cyanobacterial and photosynthetic bacterial photosynthesis.

Figure 2A:
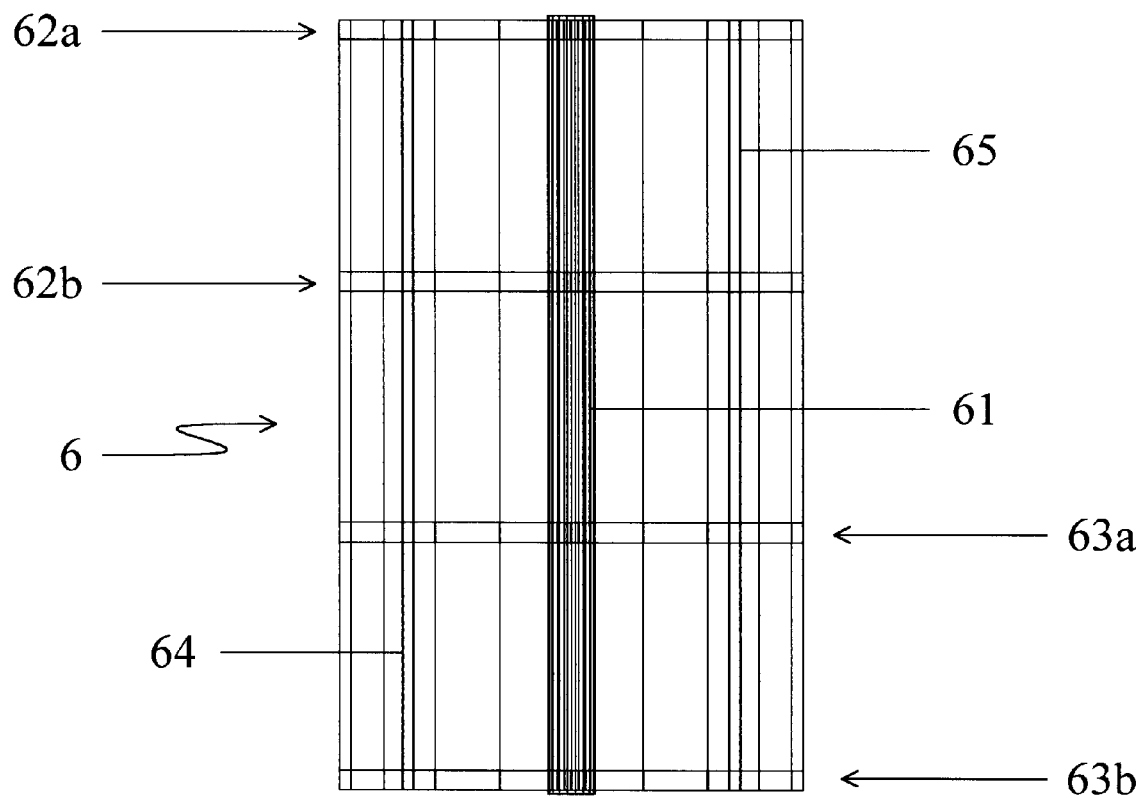
FIGS. 2a, 2b, and 2c are elevational, plan, and perspective views of a preferred matrix structure for holding biomass for anaerobic digestion in the digester vessel.
Figure 2B:
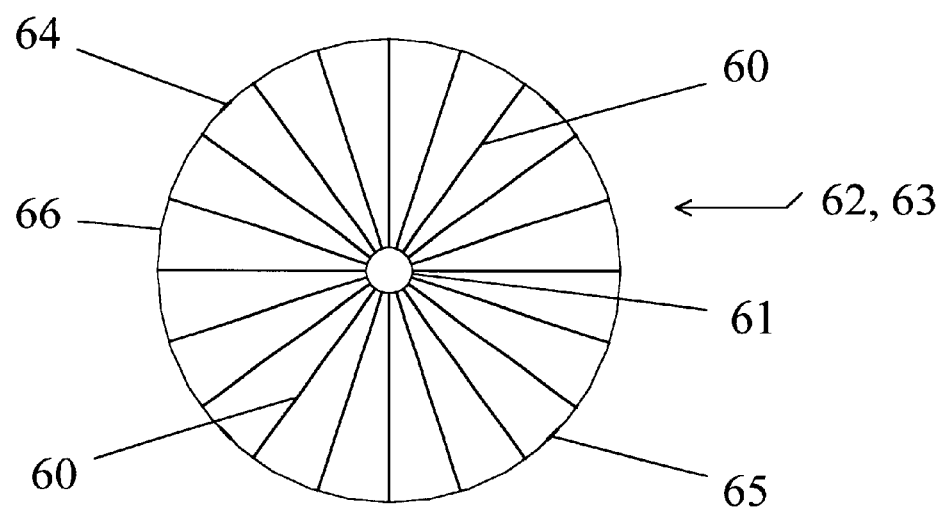
Figure 2C:
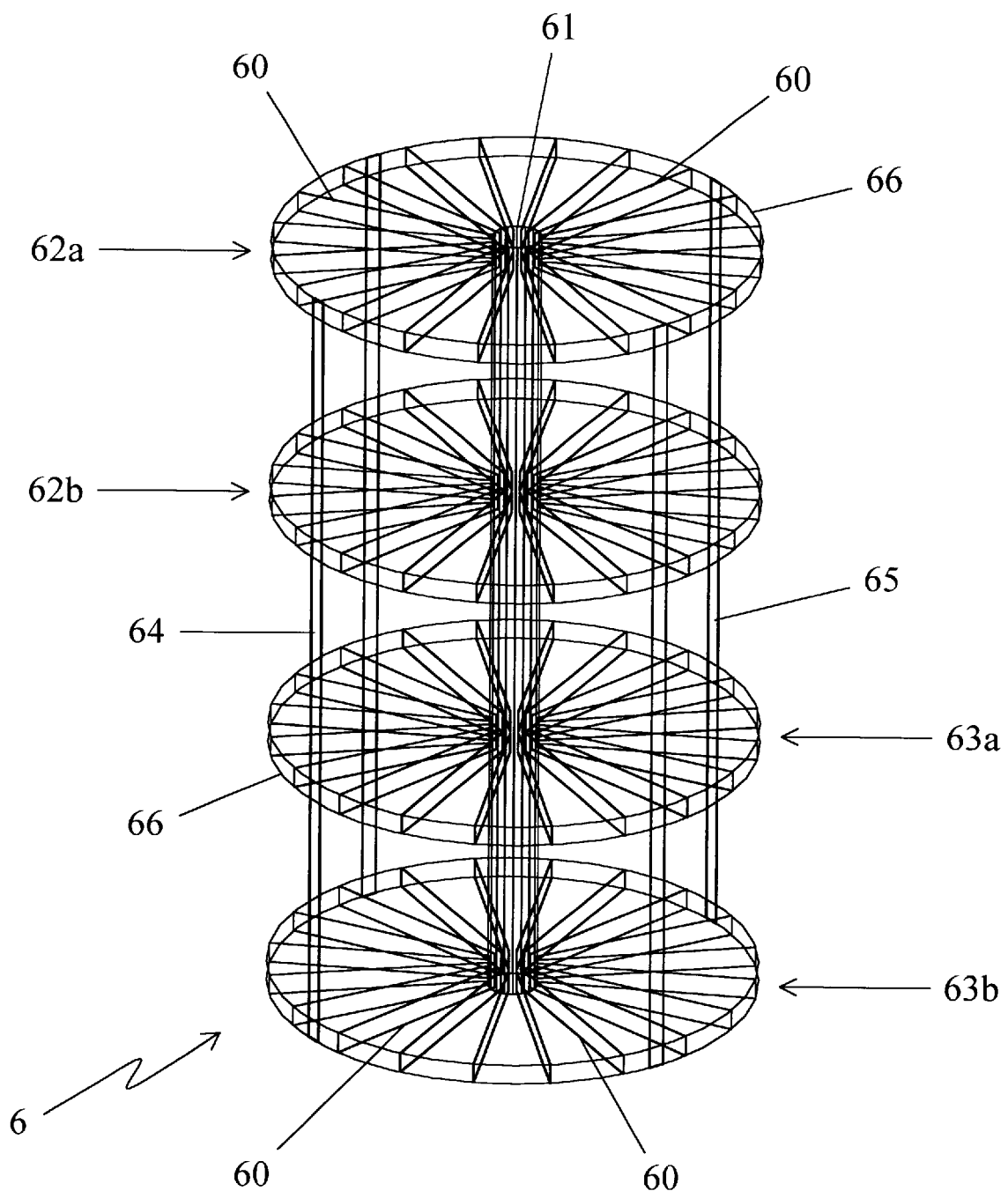

As shown in FIGS. 2a, 2b, and 2c, the matrix 6 is formed as an array of panels mounted to a hollow spindle 61 which is mounted coaxially over the standpipe 4-5 on the central axis of the vessel. The matrix 6 is supported on the vertical spindle 61 through the use of four wheels 62a, 62b, 63a, 63b at spaced intervals along the vertical height of the panels. The wheels have a number, e.g., 20, stainless steel spokes which radiate from a center stainless steel support tube of 8-inch diameter. The spokes may be formed by flat bars of ¼-inch thickness by 2-inch width. The spokes extend to rims 66 supported within 1 inch of the vessel walls. The rims have a five-foot, ten-inch diameter and may be formed with stainless steel, ¼-inch by 2-inch, curved flat bars. Each wheel is stabilized on the outer perimeter by four welded flat bars 64, 65 (¼-inch by 2-inch) welded at 90-degree arc intervals to and extending the full length of the spindle. At the top wheel, a split 1-inch diameter polyvinyl chloride (PVC) pipe is placed over each stainless steel spoke to act as a wear-reducing sleeve for the matting to be placed over them.

The preferred biomass-immobilizing matrix is formed with flexible planar surfaces having a three-dimensional surface architecture. These surfaces are formed with variegated surface elements that have a large combined surface area onto which the biomass material becomes attached. A particularly advantageous material is MONSANTO (™) polyethylene (artificial) grass matting (manufactured without biocide), such as are typically used for entry mats. The artificial grass is composed of evenly spaced, approximately 12 mm. on centers, tufts of tapered grass blades or fingers, protruding from the perimeter of a 4.0 mm diameter cup, about 3 mm deep. Each grass blade or finger is approximately 20 mm long, 2 mm wide, and 0.3 mm thick, and is bent in random orientation by application of heat during manufacture to effect a grass-like appearance.

The immobilizing matrix material must be relatively charge free and manufactured of material which remains uncharged when submerged in aqueous solution. Polypropylene and polyethylene are two plastic materials having polymer chains of methyl ($CH_3$) groups or hydrogen protons (H), respectively, that can be manufactured with a low surface charge characteristic. The low surface charge avoids binding other materials that will blind off the active biomass from the digestion process. The MONSANTO (™) grass matting provides an ideal combination of high surface area, durable construction, and low bonding charge at the surface.

The grass matting is applied on the matrix in long sheets from one spoke of the bottom wheel on one side, passes up the spindle, wraps over the PVC sleeve on the spoke of the top wheel and extends back down to the same spoke at the bottom wheel. Each vertical column of spokes supports two mat surfaces bound back-to-back by polypropylene ties, which are pierced and looped through the mat surface and around the metal support members. The matting is reinforced with a heat-bonded fiberglass scrim on the back.

The biomass can be discreet cells, colonies, or aggregates of cells, cells of organisms moved to the surface by microdiffusion of gasses, or attached cells on immobilizing matrices. The prior art, for example, U.S. Pat. No. 4,919,813 to Weaver, disclosed adding photosynthetic bacteria to the fermentation to accelerate the slow step of acetate conversion to methane, and used translucent covers for such digesters. However, in the present invention, it is found that photosynthetic bacteria are naturally present in most if not all waste streams indicating they do not need to be added to fermentation for their activity to be present and enhanced by light. These bacteria are facultative, i.e., able to grow in air or anaerobically. Their activity is enhanced by incidental light, and if light is provided (most anaerobic digesters are dark reactors), they will provide additional energy in the fermentation in the form of ATP (adenosine triphosphate).

A vessel of the dimensions described, without the inclusion of matrix material, would have a gross surface to volume ratio of 0.8 to 1. The vessel with plain film arrayed on the spokes would have a gross surface area to volume ratio of 4 to 1. In contrast, the vessel with the grass matting arrayed in this fashion is calculated to have a surface area to volume ratio of 20 to 1. The radial array of mats ensures that the opposing grass surfaces do not make contact with each other. The spacing between opposing surfaces is such that there is sufficient space from the center post to the outer diameter of the matrix for the high solids of the digestion to flow without clogging the channels between them.

The hollow spindle 61 is sleeved over the central standpipe and rests on a center core ring brace placed at a position even with the top of the 45-degree cone base. Four side brace blocks are held by fiberglass bonding at 90-degree spacing around the perimeter of the tank in a common plane with the center ring support to provide for outer ring support. The spindle 61 extends above the liquid surface of the operating fermentation liquid and into the wet gas headspace of the vessel. The grass mat panels of the matrix 6 divide the working fermentation fluid into discrete pie shaped sections or channels.

Anaerobic Digester Process Flow

Figure 3:
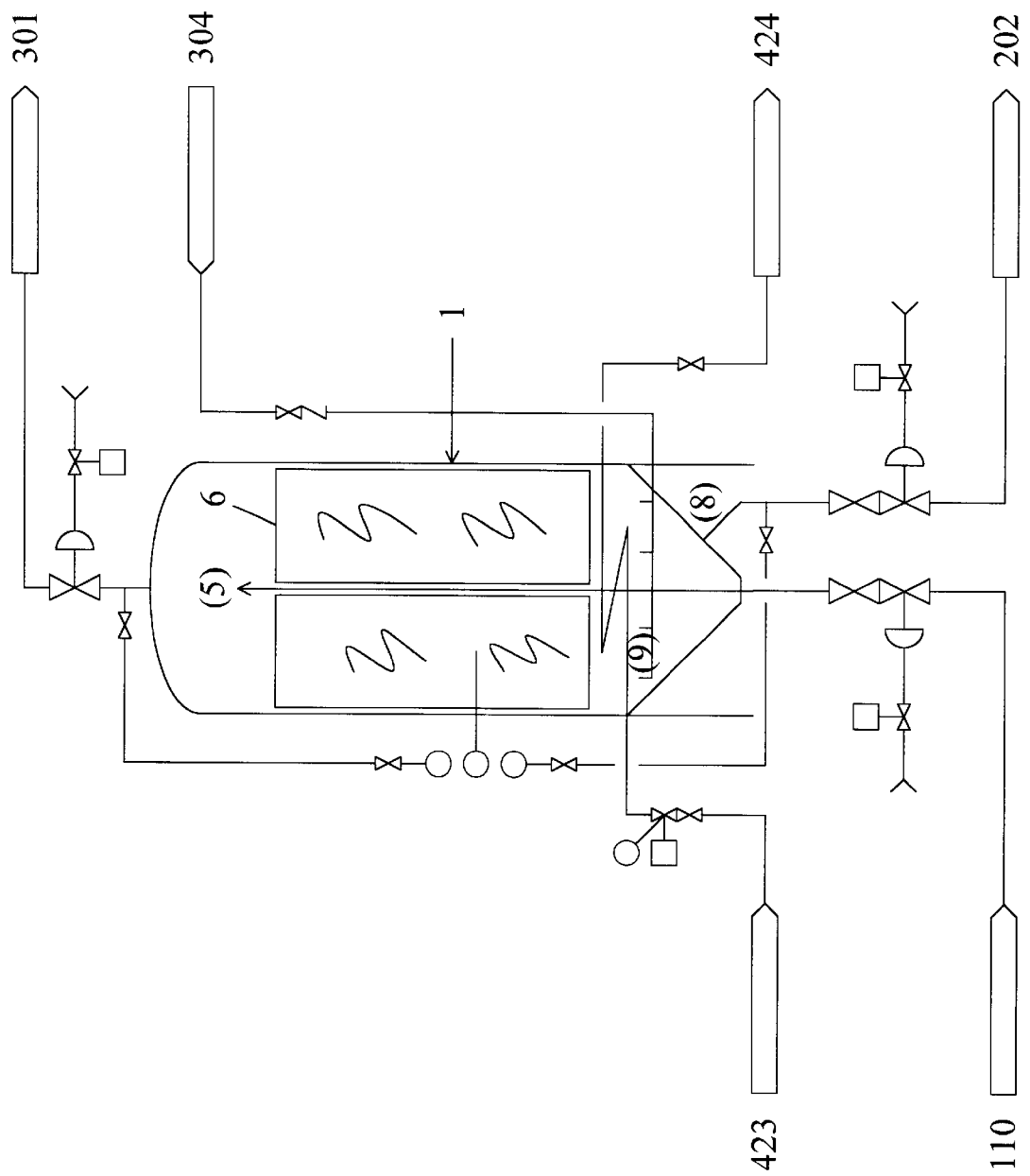
FIG. 3 is a schematic diagram of the components of the core anaerobic digester system in accordance with the invention.

In the use of the preferred digester vessel embodiment of the invention, as illustrated in FIG. 3, the anaerobic digester process flow obtains high suspended solids digestion within the vessel 1 in a vertically downward flow by supplying a liquid slurry feedstock from an input process 110 through the vessel inlet 5 at the top of the vessel to flow downwardly over the biomass-supporting digester surfaces of the matrix array 6. For the input process 110, wastes are comminuted by the action of a slurry grinder and recirculated and processed into a pumpable slurry. Preferably, the input slurry is 8–10% by weight (80,000–100,1000 mg per liter) solids, of which 90% are suspended solids of maximum particle size of 6–7 mm wide by 10–15 mm length.

During startup of the system, a bacterial inoculum from various sludge sources is added to the biomass slurry as 10% of the volume. This can be sludge from wastewater sumps from animal or agricultural operations such as dairy, cattle, feeder cattle, swine, or digester sludge from municipal wastewater treatment systems. The first total volume loaded is inoculated in such a manner.. For the first 60 days of startup, such bacterial solids residue as collected from the filter screening process is reapplied at a 10% rate, thereby ensuring sufficient acclimatized bacteria in the feedstock slurry. The bacteria inoculum as described generally has sufficient quantities of the types of bacteria needed for the bioconversion process as described herein.

Gas generated by the digester process is collected and supplied from the top of the vessel to a gas process 301, and also recycled from gas process 304 back into the vessel to gas diffuser 9 as a mixing means for the slurry (described below). Fluid from heat exchange HX supply 423 is circulated in the heat exchange coils 11 and exits to HX return 424. An output solids byproduct slurry is withdrawn through vessel outlet 8 to an output process 202.

The four basic stages of anaerobic digestion to produce a methane byproduct are: (1) hydrolysis of large particulate solids; (2) fermentation of large polymers into intermediates, i.e. acids and alcohols; (3) conversion of these acids and alcohols into carbon dioxide, hydrogen and small chain fatty acids, e.g. acetates; and (4) reduction of carbon dioxide, hydrogen and acetates into methane. Hydrolytic bacteria are used as the digestive biomass to produce enzymes for the breakdown of all of the various solids into smaller particles, then liquids releasing carbon dioxide and hydrogen into the fermentation liquor. The enzymes produced by the hydrolytic bacteria cleave the large polymers of cellulose, protein, and fat.

In the preferred embodiment, the hydrolytic bacterial population is immobilized on the matrix 6 to have intimate contact with the feedstock, and the biomass population produces exoenzymes or endoenzymes to hydrolyze solids in the feedstock. The type of substrate or feedstock triggers the appropriate enzyme production. As a result of hydrolysis by enzymes, these macromolecules are reduced in size, buoyancy, and weight and charge characteristics. These smaller molecules move up the hydraulic column and are further hydrolyzed by other hydrolytic bacteria. Gaseous byproducts of the various stages of digestion form as very minute micro bubbles inside the individual cell's cellular membrane and on the extracellular membrane surface and provide for movement vertically in the column acting as a natural mixing means.

The immobilizing matrix 6 allows for increased cellular population density, producing increasing numbers of microbubbles which, aided by their proximity to each other, coalesce into larger bubbles. These larger bubbles, with increased buoyancy, move toward the surface of the column moving larger particulate and polymers with them, thereby mixing the slurry and exposing the polymers and particles to the respective sites of hydrolytic enzymatic activity, all the way toward the top of the column at the initial input level.

Fermentative bacteria are responsible for the conversion of the hydrolysis byproducts into intermediate compounds. These bacteria are capable of doubling their population biomass in less than 3 to 6 hours and will respond to substrate concentrations rapidly. As these bacteria convert intermediate products of hydrolyzed solids into alcohols and acids, the fermentation can become acidic. If the pH falls below 6 in anaerobic digesters, typically the fermentation and digestion is inhibited from going further due to the very activity of the acid producing bacteria. If present in the fermentation in high enough concentration, acetogenic bacteria are able to convert these alcohols and acids into acetate, carbon dioxide and hydrogen. This can be improved by the presence of the immobilizing matrix.

The final phase of digestion requires a population of methane-making organisms, methanogens, to be present and sufficiently abundant enough to convert the various byproducts of the acetogens, i.e. acetates, carbon dioxide and hydrogen into methane. Methanogens, the bacteria making up the majority of the class of archeobacteria, referred to as extremophiles, are only capable of doubling their population at a very slow rate of 192 hours. However, the various eubacteria represented by the hydrolytic, fermentative and acetogenic types of bacteria, responsible for the previous stages of digestion are able to double their respective populations 60 times faster. This difference in growth rates produces the aforementioned imbalance in cellular byproducts. This deficient rate of growth of the methanogens is overcome in the invention by provision of the matrix enabling its stable immobilization. The immobilizing matrix sustains an increased density of slow growing methanogen populations in the fermentation column.

The immobilized population of the types of bacteria responsible for complete digestion of particulate solids in the feedstock slurry are active in byproduct conversion and as a result increase the bicarbonate alkalinity, to a level approaching 10 grams per liter, thus providing sufficient natural buffer to continually digest biomass with a pH as low as 4.5, especially highly acidic fruit wastes, including the acidity resulting from rapid conversion of sugars and starches. The usual corrective measures available for sour digesters without the immobilizing matrices is either by dilution of the total contents of the vessel with spent digester effluent (unavailable from the sour digester) with sufficient alkalinity, or by the addition of chemicals, i.e., caustic soda, caustic lye or hydrated lime to adjust the pH artificially. The addition of chemicals for adjustment adds operational costs and is problematic in anaerobic digestion due to the adsorption and indiscriminate bonding of these chemicals to cell membranes thereby affecting cell diffusion or to active enzymatic sites of the intermediate by-products of digestion.

In the preferred embodiment, acclimated bacteria, specifically the acetogens and the methanogens, are encouraged to grow to a sufficient population density on immobilizing matrices within the liquid column such that the population of acetogens and methanogens is able to keep pace with the acid production of the fermentative organisms, and no artificial pH adjustments are required, and the digestion proceeds, uninhibited.

As a further feature of the present invention, the byproduct gas generated by the digester process is recycled and used as a mixing means for the slurry in the vessel. The gas is pressurized by low-pressure blower and delivered to the vessel contents through a gas diffuser or sparger 9. The sparger can be made of a flexible rubber type membrane perforated with regularly spaced 2 mm length slots supported by a 2-inch diameter, 24-inch long slotted stainless steel cylinder, interconnected in a square array at a position below the spindle of matrix panels and below the heat exchange coils 11. The membrane can be made of inert rubber or plastic to prevent clogging and/or plugging of the pores or orifices due to bacterial growth. These pores open under pressure to allow for diffuse microbubble mixing.

Turbulent mixing produces a surface boil, often resulting in foam. This is the result in some sewage treatment anaerobic digesters where gas spargers are used as a mixing medium. Foam is considered to be a dangerous nuisance, it can fill the head space, and can eventually pass into the gas collecting header causing plugging of the gas outlet and requiring increased maintenance. Foam can even upset the heavy floating covers of sewage digesters by flowing up and on to their tops causing an imbalance in their position. A surfactant or antifoaming agent is then required to be added to the digestion to reduce foaming which would be caused by turbulent gas mixing. The antifoam or surfactant would also be detrimental to immobilization of bacterial cells.

Figure 4:
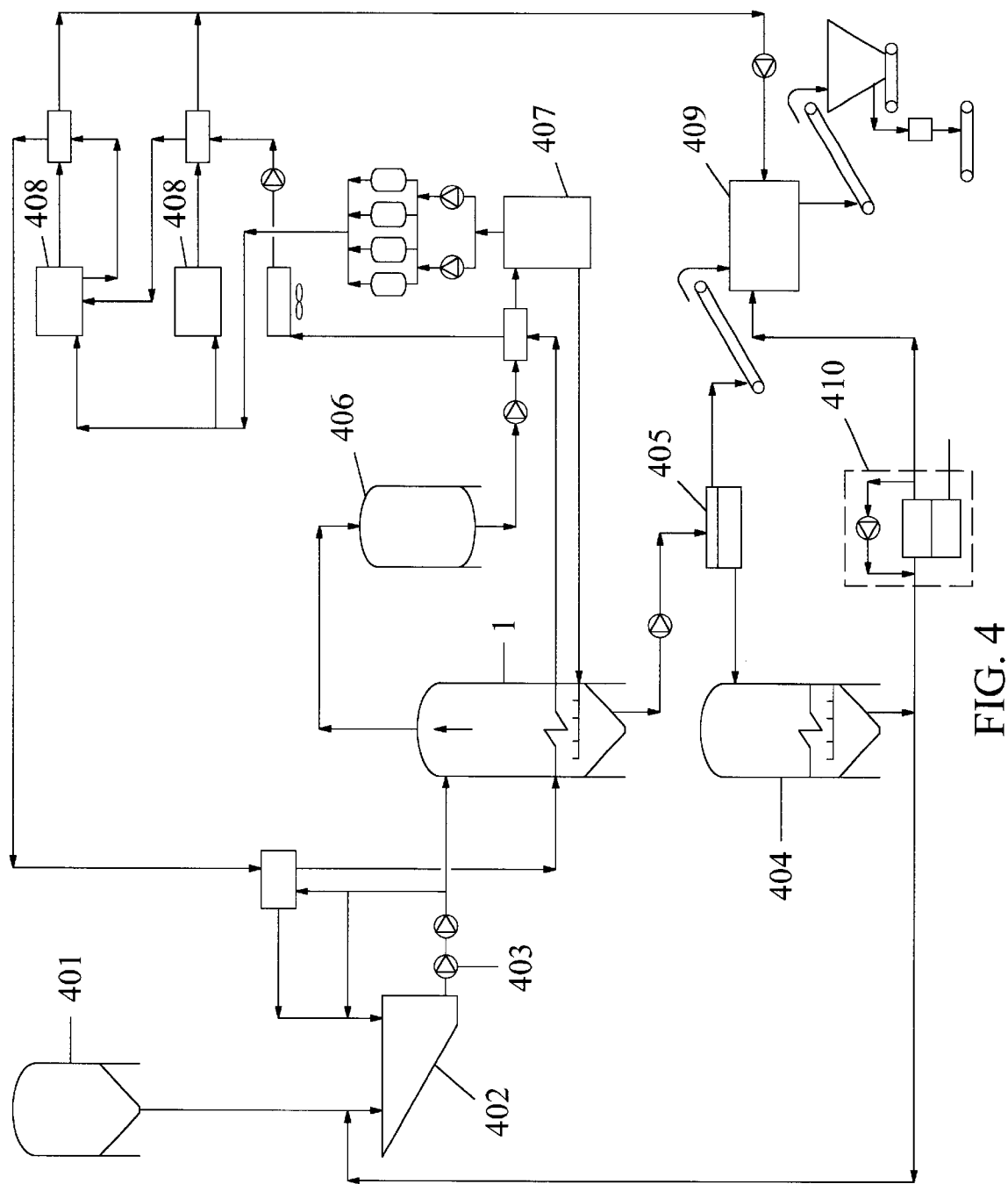
FIG. 4 is a schematic diagram of other system components for the anaerobic digester system.

As illustrated in FIG. 4, the anaerobic digester system includes other components which support the main process. A storage tank 401 holds the input wastes to be processed. A mix tank 402 and grinder 403 comminute and supply the input feedstock slurry to the digester. A surge tank 404 holds liquid from the vessel effluent output passed through a screen filter 405 for addition of liquid to the mixing tank. An $H_2S$ scrubber 406 removes sulfide from the output gas, and a membrane separator 407 separates a methane gas product from the gas volume. The remaining gas is returned to the vessel for use in the spargers for generating gas turbulence for mixing in the vessel. Some of the methane gas product may be used to power the generator engines 408 to generate electricity used throughout the system and heat for the heat exchanger system. The heat exchanger system includes the supply of heated fluid to the heater coils in the vessel. The screened-off solids from the output effluent can be concentrated and dried in a dryer 409 for bagging as a soil additive product. An ultrafilter is used to separate bacterial solids as a plant food and a residual filtrate which can be used as a plant tonic. A portion of the bacterial solids is discharged to the mix tank 402 periodically during startup to innoculate the immobilizing matrix.

Anaerobic Digester Process Parameters

In the following description, certain terms are used which are commonly understood in the industry. These are explained as follows.

Total Solids (TS)

All organic matter contains some water. The human body is approximately 70% water. Total Solids (TS) is a measure of the actual solid content of a substance. TS is determined by weighing a sample, oven-drying it to remove all moisture, and then re-weighing the dried sample. TS % is determined by dividing the "dry" weight by the "wet" weight. The same human body is therefore 30% TS.

Volatile Solids (VS)

VS is a measure of the solids (portion of TS) which are actually available for bioconversion. VS is determined by "burning" the dried TS sample, which removes the "volatile" component. What remains is non-volatile (see NVS below). The sample is weighed again to determine this "ash" weight, which is subtracted from TS to determine VS. VS % is found by dividing VS by TS.

Non-Volatile Solids (NVS)

NVS is what remains in a sample after removing the VS in a furnace. NVS (mostly minerals in ash form) are not bioconvertible. NVS % is determined by dividing NVS by TS.

Hydraulic, Solids, and Microorganism Retention Time(s) (HRT, SRT, MRT)

Retention time refers to how long a given material is kept (retained) in the system. Typical units are in days. Hydraulic Retention Time (HRT) measures the length of time that liquid remains in the system. HRT is determined by dividing system volume by feedstock volume. Solids Retention Time (SRT) is the length of time that feedstock solids remain in the system. An Upflow Solids Reactor (USR) retains the solids longer than the liquid (SRT>HRT). Microorganism Retention Time (MRT) is the length of time that the anaerobic bacteria (microorganisms) remain in the system. Longer MRT's, which can be achieved by using a growth matrix, promote increased system stability, while simultaneously reducing nutrient requirements (see below).

Organic Loading Rate

Organic Loading Rate is a measure of the organic material (VS), per digester volume, added to the system on a daily basis. The units are in kg of $VS/m^3$-day. The value is determined during engineering. For a given system size, higher organic loading rates generally result in lower digestion efficiency. Any value greater than 3.3 kg $VS/m^3$-day is considered high-rate digestion.

Methane Yield

Methane Yield is a measure of the quantity of methane produced from the VS which are added to the system. The units are in $m^3$ of $CH_4$ per kg of VS added. The value is dependent upon the type and digestability of the feedstock and the retention time in the system. It is also affected by the condition of the digestion (raw gas quality). 1 kg of VS that is 100% digested into 100% methane would yield 1.4 $m^3$. More typically, 1 kg VS is 70% digested into 65% methane, yielding 0.4 $m^3$.

Methane Production Rate

Methane Production Rate is a measure of the quantity of methane, per digester volume, generated by the system on a daily basis. The units are in m3 of $CH_4$ per $m^3$-day. A value of 1 $m^3$ $CH_4/m^3$-day is reasonable. Methane production rates are proportional to the sulfur required for digestion, because more $H_2S$ is carried away during vigorous gassing.

Chemical Oxygen Demand (COD)

COD is a parameter which provides an estimate of the quantity of organic material in a sample. The units are in mg/l. The value returned is dependent upon the sample being tested. Samples of feedstock may measure 100,000+mg/l, while filtrate samples are generally around 2000 mg/l. The test itself is an EPA-approved method which provides faster, more repeatable results than the more common Biological Oxygen Demand (BOD) test.

Bicarbonate Alkalinity

Bicarbonate alkalinity is a parameter by which the buffering capacity of the general biochemistry of a fermentation is measured. This is usually due to the solubilization of carbon dioxide resulting from the digestion or conversion of organic wastes. Acid is usually formed as intermediary compounds. To the degree sufficient bicarbonate alkalinity is present, high loading rates of solids to the digestion can occur without the need to adjust the pH.

Volatile Acids Concentration

Volatile acids are measured to determine the equivalent buffering capacity which may be needed in the fermentation or digestion. The relative concentration of volatile acids affects the overall pH. If the volatile acids concentration exceeds the ability of the bicarbonate alkalinity present to maintain the pH above 6.5, then the fermentation turns acid and methane formation ceases.

A typical example is provided of the calculation of operating parameters for the digester process, based upon an input of food waste slurry as feedstock. The first step is to define the feedstock. Analyses are conducted to determine TS and VS, and amounts for the nutrients nitrogen, sulfur, phosphorous, iron, cobalt, nickel, molybdenum, and selenium. Once TS % is known, the batch size and system volume can be established. Batch TS % should be kept below 9%, due to processing equipment limitations. The following provides an example using 1000 kg of food waste:

| | |
|---|---|
| Total Weight of Material | 1000 kg |
| Food Waste TS % | 10% |
| TS in Food Waste | 100 kg |
| TS % of Batch | approx. .08 (8%) |
| Batch Size | 1250 kg or liter |
| HRT of System | multiplied by 30 days |
| Required System Volume | 37500 liter |

The Organic Loading Rate is determined using TS, VS %, and System Volume, as follows:

| | |
|---|---|
| TS in Food Waste | 100 kg |
| VS % of TS | multiplied by 0.9 (90%) |
| VS in Food Waste | 90 kg |
| System Volume | approx. 37.5 m$^3$ (1000 l/m$^3$) |
| Organic Loading Rate | 2.4 kg VS/m$^3$-day |

An example of batch digestion is conducted as a test to determine feedstock digestability and gas quality (density). These parameters are used to calculate Methane Yield:

| | |
|---|---|
| VS in Food Waste | 90 kg |
| Digestion Efficiency | multiplied by 0.8 (80%) |
| VS Converted | 72 kg |
| Gas Density | approx. 1.14 kg/m$^3$ (@ 65% CH$_4$) |
| Total Gas | 63.2 m$^3$ |
| CH$_4$ (Methane) % | multiplied by 0.65 (65%) |
| Total Methane | 41.1 m$^3$ |
| Methane Yield | .46 m$^3$ per kg VS added |

Methane Production Rate is determined using the Total Methane and System Volume:

| | |
|---|---|
| Total Methane | 41.1 m$^3$ |
| System Volume | approx. 37.5 m$^3$ |
| Methane Production Rate | 1.1 m$^3$/m$^3$-day |

In addition to the energy (in the form of carbon C) in the VS, the bacteria require certain nutrients to be able to bioconvert energy. These nutrients are successively limiting. That is, enough of one nutrient must be available in excess for a subsequent nutrient to provide any improvement in process efficiency. An example of the calculation of amounts of nutrients is provided below.

The nitrogen (N) requirement is 1 kg N per 60 m$^3$ of methane gas, or 6 kg N per 1000 kg COD. It is six times greater for carbohydrate digestion than for proteins and fatty acids. For 1000 kg of food waste (41.1 m$^3$ methane), the nitrogen requirement is calculated as follows:

| | |
|---|---|
| Total Methane | 41.1 m$^3$ |
| Methane per 1 kg N | 60 m$^3$ |
| Required N | .69 kg |

The amount of sulfur required is related to the Methane Production Rate. It is essentially equal to the nitrogen requirement. For optimum digestion, the head gas should contain 0.5% H$_2$S, or approx. 23 mg/l dissolved sulfide.

The phosphorous requirement is approx. 15% of the nitrogen requirement, i.e., .69 kg×0.15, or about 0.10 kg.

The proportions of iron, cobalt, nickel, molybdenum, and selenium required are 10 mg/l Fe, 5 mg/l Co, and 0.1 mg/l of Ni, Mo, and Se:

| | |
|---|---|
| Batch Size | 1250 kg or liter |
| Fe Ratio | 10 mg/l |
| Required Fe | .0125 kg |
| Co Ratio | 5 mg/l |
| Required Co | 6250 ppm |
| Ni, Mo, Se | .1 mg/l |
| Required Ni, Mo, Se | 125 ppm |

For feedstock preparation, input wastes are combined with additional liquid in a mixing device (hydropulper) to form a slurry through particle size reduction. The resulting feedstock is generally limited to approximately 9% TS, due to processing equipment considerations. Once the "batch" is complete, it is loaded into the Anaerobic Digester with a pump, passing through a trash removal filter for contaminant removal.

The gasification (digestion) of the feedstock is performed in the anaerobic digester. This process is affected by several distinct groups of bacteria working in concert. The first group, hydrolytic bacteria, break down organic compounds to fermentation products, such as organic acids, alcohols, and CO2. The second group, transitional bacteria (acetogenic, homoacetogenic), convert the products of the first group to acetate, hydrogen, and CO$_2$. These are the products which are actually converted to CH$_4$ and CO$_2$ by the third group, methanogenic bacteria. Each group relies on the next to consume its products, which prohibits inhibition that occurs when excess concentrations of these compounds are allowed to develop.

Anaerobic Digester Products

The products of the anaerobic digester process include the gas produced, which contains approximately 65% CH$_4$, 34%

$CO_2$, 0.5% $H_2S$. For the output gas process, the gas product is "scrubbed" to remove the $H_2S$. With equipment modification, the clean methane gas product may be utilized in engine generators, cooking and/or refrigeration appliances, gas burners, etc. The gas product may also be further processed into methane vehicle fuel (CNG), for replacing gasoline or diesel fuel, by removing the $CO_2$ with a membrane separation system.

Since bioconversion is never 100% efficient, there are non-converted and non-convertible solids (VS and NVS) remaining in the effluent from the system, which can be further processed into other output products. For the output effluent process, effluent is pumped over a vibrating screen to remove "coarse" solids. These are placed in a dryer for pasteurization and moisture adjustment. The resulting solids product can be used as an organic soil amendment, which may be packaged in bags for sale. The screened effluent is further processed with an ultrafilter. This device separates bacterial solids from the liquid and dissolved solids. The concentrated bacterial solids can be used as a plant food, may be packaged in bottles for sale. The "filtrate", a plant tonic, may be stored and shipped in bulk to commercial users.

The following is an example of use of the anaerobic digester processing to generate methane gas for use as an energy co-generator. The maximum (generator) demand is assumed to be 150.5 $m^3$ per day, or 5315 cfd (cubic feet per day). Excess gas should be available, because the generators will rarely be at 100% load. This works out to the following parameters, assuming the raw gas composition is 70/28/1 and 87% of the $CO_2$ (26 $m^3$, 51.4 kg) is converted to $CH_4$ (71 $m^3$, 50.9 kg):

| | |
|---|---|
| Input Load: | 1700 kg (per batch, semi-continuous) |
| Volume | 1717 liters |
| Percent Solids | 10.9% |
| Total Solids | 185 kg |
| Volatile solids | 90% = 167 kg |
| Organic Loading Rate | 3.5 kg VS per $m^3$-day |
| Digestion Rate | 3.3 or greater |
| Conversion rate | 72% = 120 kg |
| Process Volume | 6814 liters/vessel × 7 vessels = 47696 liters |
| HRT | 27.8 day |
| Surge Tank Volume | 3777 liters |
| HRT | 2.2 day |
| HRT Total | 30 day |

The methane gas product is a medium-BTU gas. It may be utilized in a variety of applications, between which there are fairly linear cost-benefit or risk-reward relationships. It may be consumed in an engine generator to produce electricity. Typically, this is the lowest value/risk option. The revenue from such use is dependent upon prevailing local rates and how the produced electricity is distributed. Generally, the electricity would be sold at a wholesale rate to the local utility through an independent meter. Such arrangements/rates are governed by an area's utility commission. "Net" metering (exporting electricity through an existing meter for the "retail" rate) is not yet a reality, although it has begun to be considered in areas around the country. One way to realize greater value for the power is to provide it "in-house", thereby reducing the amount of electricity which would otherwise need to be purchased. The best loads for consideration are "lighting only" or "motor only" types where the decreased-quality power provided by a generator set will not negatively impact personnel or operations.

With equipment modification, the gas product may replace the use of propane or natural gas in cooking, heating, refrigeration and/or lighting. This provides increased value (when replacing propane), but also presents the highest risk because, once converted, the selected equipment won't be able to use it's original fuel unless it is "converted back". However, some equipment can be converted or purchased to use two types of fuel (bi-fuel), which would preserve the equipment's function, even if one fuel source was interrupted.

With further processing, the gas product can replace standard transportation fuels. Vehicles can be purchased or converted to use gas as fuel, instead of gasoline or diesel. This use presents the one of the greatest values, both economically and environmentally. There is risk associated with this choice, but it is less than when using the gas in stationary equipment. Such risk can be minimized by converting to or purchasing vehicles which are capable of "bi-fuel" operation (as with appliances). Our fossil-fuel-based economy is rapidly depleting its reserves. Also, for every conversion step, there are associated losses (efficiencies). Pollution is inversely proportional to energy efficiency. The least efficient (most polluting) use of energy is as gasoline for vehicle fuel. The least efficient use of non-renewable energy can be replaced with the renewable energy gas product to provide the greatest environmental benefit as well as an economic return.

For the soil addition product, the fibrous, undigested solids are screened and conditioned into a low nutrient amendment similar in appearance to compost, yet superior in function. It can be used in a variety of ways, including amending, fertilizing, mulching, dressing, planting, etc. Depending on the feedstock materials, sufficient nutrients may remain in the soil additive to qualify it as a fertilizer (N+P+K=>6). This would increase the market value of the product dramatically. Filter-separated bacterial biomass may also be recombined with the soil additive to result in a more valuable product (enhanced nutrient content).

The process of the anaerobic digestion could also be described as bacterial "agriculture", . As the bacteria consume the feedstock, they grow and multiply, eventually die off and are removed in the effluent stream. These organisms are a source of high quality protein, which can be captured by separating the bacterial biomass from the screened effluent with a filter. The "emulsion" from filtering is then directed to a dryer to remove most of the remaining moisture. The resulting "protein powder" contains significant levels of amino acids, peptides, and growth factors, which makes it an excellent feed additive for agri- or aquaculture.

Liquid co-products are also available from anaerobic digestion. A plant tonic can be provided as a bacteria-free liquid nutrient with soluble vitamins and ammonia nitrogen for fast absorption by plants and for algae culture. After filtering, the separated bacteria may also be used as an effective plant food. The "emulsion" contains primarily organic nitrogen, which is slowly made available to plants following application to the soil.

The following tables provided typical analysis of the composition of solid and liquid products form the anaerobic digestion process for a mixed input on a dry weight basis of 50% food waste, 25% green waste, and 25% paper waste following 28 days digestion:

TABLE 1

BYPRODUCT ANALYSIS: SOIL ADDITIVE (DRY WEIGHT BASIS)

| NUTRIENT | SOIL ADDITIVE % |
|---|---|
| Total Nitrogen | 2 |
| Ammonium Nitrogen | 1 |
| Amino Acid Protein | 6 |
| Crude fiber | 50 |
| Crude Fat | 3 |
| Ash | 12 |
| Phosphorus | 0.5 |
| Potassium | 1.5 |
| Calcium | 2 |
| Magnesium | 0.3 |
| Iron | 0.3 |
| Sulfur | 0.5 |

BYPRODUCT ANALYSIS: BACTERIAL EMULSION (DRY WEIGHT BASIS)

| NUTRIENT | BACTERIAL EMULSION % |
|---|---|
| Total Nitrogen | 8 |
| Ammonium Nitrogen | 2 |
| Amino Acid Protein | 37 |
| Crude fiber | 10 |
| Crude Fat | 9 |
| Ash | 25 |
| Phosphorus | 1 |
| Potassium | 2.5 |
| Calcium | 3 |
| Magnesium | 0.6 |
| Iron | 1 |
| Sulfur | 1 |

BYPRODUCT ANALYSIS: PLANT TONIC (DRY WEIGHT BASIS)

| NUTRIENT | PLANT TONIC % |
|---|---|
| Total Nitrogen | 35 |
| Ammonium Nitrogen | 25 |
| Amino Acid Protein | 10 |
| Crude fiber | 1 |
| Crude Fat | 2 |
| Ash | 60 |
| Phosphorus | 4 |
| Potassium | 30 |
| Calcium | 2 |
| Magnesium | 2 |
| Iron | 0.1 |
| Sulfur | 2 |

LIQUID NUTRIENT PROFILE

| NUTRIENT | PERCENT | DRY WEIGHT (lbs. per 1000 gals) |
|---|---|---|
| Nitrogen | 0.4 | 33 |
| Phosphorus | 0.08 | 6 |
| Potassium | 0.15 | 12 |
| Calcium | 0.06 | 4 |
| Magnesium | 0.03 | 2 |
| Sulfur | 0.02 | 1 |

TABLE 2

AMINO ACIDS IN BACTERIAL EMULSION

| AMINO ACID | PERCENTAGE |
|---|---|
| Arginine | 4.52% |
| Histidine | 3.18 |
| Isoleucine | 5.65 |
| Leucine | 9.03 |
| Lysine | 3.95 |
| Methionine | 2.11 |
| Cystine | 1.98 |
| Phenylalanine | 5.86 |
| Threonine | 4.80 |
| Tryptophan | 0.56 |
| Valine | 6.28 |
| Alanine | 7.34 |
| Aspartic acid | 9.46 |
| Glutamic acid | 14.82 |
| Glycine | 7.06 |
| Proline | 5.65 |
| Serine | 4.94 |
| Tyrosine | 2.75 |

A typical commercial bioconversion system using an array of the above-described digester vessels would be capable of processing daily in the range of 92 metric tons of garbage biomass, comprised of 80 kilotons of food waste, 8 kilotons of paper, and 4 kilotons of fats, oils, and grease (FOG). A daily volume of 172,000 liters (45,000 gals.) which is 9% TS is processed into a total volume of 4.8 million liters (1.3 million gals.) contained in 16 vessels. The daily byproducts, after a 60 day startup period, would be in the range of 5700 cubic meters of methane, 4.5 dry kilotons of soil additive, 42,000 (11,000 gals.) bacterial emulsion, and 98,000 liters (26,000 gals.) dilute liquid fertilizer.

It is understood that many modifications and variations may be devised given the above description of the principles of the invention. The digester vessel can be constructed in a wide range of sizes and other structural materials. The biomass matrix can be formed with other structures, such as screens, vanes, racks, etc., and the immobilizer surface can be made of other suitable materials. The process parameters can vary depending on the composition of the input wastes, the processing rate or volume desired, and/or output products desired. A digester vessel may be combined with other digester vessels in an array or in stages for a wide range of bioconversion applications. It is intended that all such modifications and variations be considered as within the spirit and scope of this invention, as defined in the following claims.

I claim:

1. An anaerobic digester system, comprising:

a vertically upright cylindrical vessel having a given vessel diameter, a support matrix arranged in a cylindrical core portion of the vessel for supporting a microorganism biomass thereon, wherein the support matrix includes a plurality of vertically-oriented radial panels spaced at angular intervals within the vessel, said panels having planar surfaces with a three-dimensional surface architecture for supporting the microorganism biomass thereon, a vessel input for supplying an input slurry feedstock of liquid containing anaerobically digestible solids at an upper portion of the vessel above the matrix, a gas output at the upper portion of the vessel for withdrawing an output gas from the vessel generated by anaerobic digestion of the solids in the feedstock by the microorganism biomass, and an effluent output at a lower portion of the vessel below the matrix for withdrawing liquid and remaining solids from the lower portion of the vessel;

wherein the vessel contains liquid to a height around the support matrix which provides a ratio of 2 to 1 of liquid height to vessel diameter in the vessel.

2. An anaerobic digester system, comprising:

a vertically upright vessel formed with core, upper and lower portions having walls constructed of inert fiberglass-reinforced plastic, a support matrix arranged in the core of the vessel for supporting a microorganism biomass thereon, wherein the support matrix includes a plurality of vertically oriented panels spaced at intervals within the vessel, said panels having planar surfaces with a three-dimensional surface architecture for supporting the microorganism biomass thereon, a vessel input for supplying an input slurry feedstock of liquid containing anaerobically digestible solids at the upper portion of the vessel above the matrix, a gas output at the upper portion of the vessel for withdrawing an output gas from the vessel generated by anaerobic digestion of the solids in the feedstock by the microorganism biomass, and an effluent output at the lower portion of the vessel below the matrix for withdrawing liquid and remaining solids from the lower portion of the vessel wherein the plastic vessel walls are coated with a translucent blue gel pigment layer which filters out ambient light at wavelengths between about 260 and 700 nanometers.

3. An anaerobic digester system of claim 1, wherein the matrix is formed as an array of vertically oriented radial panels mounted to a hollow spindle mounted coaxially on a central axis of the vessel.

4. An anaerobic digester system, comprising:

a vertically upright cylindrical vessel having a given vessel diameter, a support matrix arranged in a cylindrical core portion of the vessel for supporting a microorganism biomass thereon, wherein the support matrix includes a plurality of vertically-oriented radial panels spaced at angular intervals within the vessel, said panels having planar surfaces with a three-dimensional surface architecture for supporting the microorganism biomass thereon, a vessel input for supplying an input slurry feedstock of liquid containing anaerobically digestible solids at an upper portion of the vessel above the matrix, a gas output at the upper portion of the vessel for withdrawing an output gas from the vessel generated by anaerobic digestion of the solids in the feedstock by the microorganism biomass, and an effluent output at a lower portion of the vessel below the matrix for withdrawing liquid and remaining solids from the lower portion of the vessel;

wherein the support matrix of radial panels is mounted to a hollow vertical spindle of a given vertical height mounted coaxially on a central cylindrical axis of the vessel, and wherein the matrix is supported on the spindle through a plurality of wheels at spaced intervals along the vertical height of the spindle, and said radial panels have flexible planar surfaces supported on said wheels.

5. An anaerobic digester system of claim 4, wherein the panel surfaces are made of polyethylene artificial grass matting manufactured without biocide.

6. An anaerobic digester system of claim 4, wherein the matrix is formed with panels having surfaces made of a material with a variegated three-dimensional surface architecture which provides a surface area to volume ratio of at least 20 to 1.

7. An anaerobic digester system of claim 4, wherein the matrix is formed with panels having surfaces made of a material which is relatively charge free and which remains uncharged when submerged in aqueous solution.

8. An anaerobic digester system of claim 4, further comprising a gas diffuser located in the lower portion of the vessel to which the gas output withdrawn from the upper portion of the vessel is supplied to generate bubbles to create turbulence for mixing the feedstock in the vessel.

\* \* \* \* \*